United States Patent [19]

Schmied et al.

[11] Patent Number: 4,999,345
[45] Date of Patent: Mar. 12, 1991

[54] SULFONAMIDE DERIVATIVES AND DRUGS OBTAINED THEREFROM

[75] Inventors: Bernhard Schmied, Frankenthal; Hand D. Lehmann, Hirschberg; Verena Baldinger, Heidelberg; Klaus Ruebsamen, Neustadt, all of Fed. Rep. of Germany

[73] Assignee: BASF Aktiengesellschaft, Ludwigshafen, Fed. Rep. of Germany

[21] Appl. No.: 357,266

[22] Filed: May 26, 1989

[30] Foreign Application Priority Data

Jun. 4, 1988 [DE] Fed. Rep. of Germany ....... 3819052

[51] Int. Cl.$^5$ .................. A61K 31/18; C07C 311/19; C07C 317/14; C07D 257/04
[52] U.S. Cl. ................................. 514/117; 514/381; 514/539; 514/546; 514/562; 514/604; 548/252; 548/253; 560/12; 560/145; 562/11; 562/15; 562/30; 562/430
[58] Field of Search ................. 562/430, 11, 15, 30; 560/12, 145; 548/252, 253; 514/117, 381, 539, 546, 562, 604

[56] References Cited

FOREIGN PATENT DOCUMENTS 2809377 9/1979 Fed. Rep. of Germany .
3000377 7/1981 Fed. Rep. of Germany .

OTHER PUBLICATIONS

Journal Praktische Chemie, 77, 369–382 (1908).
Journal of the Pharmaceutical Society of Japan, 70, No. 5, 51–54, (1950).
Thrombosis Research 33, No. 3, 277–288, (1984).

Primary Examiner—Werren B. Lone
Assistant Examiner—Vera C. Clarke
Attorney, Agent, or Firm—Oblon, Spivak, McClelland, Maier & Neustadt

[57] ABSTRACT

Sulfonamide derivatives of the formula I

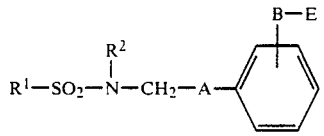

where $R^1$ is a $C_1$–$C_4$-alkyl or phenyl group which may be substituted by halogen, trifluoromethyl or $C_1$–$C_4$-alkyl, $R^2$ is hydrogen or $C_1$–$C_4$-alkyl, A is a group $CHOR^3$, C=O, C=S or C=N—$OR^4$, $R^3$ is hydrogen, $C_1$–$C_4$-alkyl phenyl, benzyl or $C_1$–$C_4$-acyl, $R^4$ is hydrogen or methyl, B may be methylene or ethylene in the m or p position or, of A is not carbonyl, may be methyleneoxy, the oxygen atom being bonded to the aromatic, and E is a carboxyl, phosphonic acid or sulfo radical, their physiologically acceptable salts, esters with $C_1$–$C_4$-alcohols or amides or the tetrazol-5-yl radical, their preparation and their use as drugs.

8 Claims, No Drawings

SULFONAMIDE DERIVATIVES AND DRUGS OBTAINED THEREFROM

The present invention relates to novel substituted sulfonamides, processes for their preparation and drugs prepared therefrom.

Substituted sulfonamides having pharmacological activity have long been known (eg. J. Prakt. Chem. 77 (1908), 369; J. Pharm. Soc. Japan 70 (1950), 283). A number of sulfonamides having lipid-lowering and platelet aggregation-inhibiting activity have also been described (eg. German Laid-Open Applications DOS 2,809,377 and DOS 3,000,377 and Thromb. Res. 33 (1984), 277).

We have found that the novel sulfonamide derivatives of the formula I

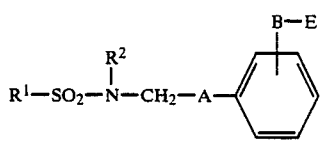

where $R^1$ is a $C_1$–$C_4$-alkyl or phenyl group which may be substituted by halogen, trifluoromethyl or $C_1$–$C_4$-alkyl, $R^2$ is hydrogen or $C_1$–$C_4$-alkyl, A is a group C=O, C=S or C=N—$OR^4$, $R^3$ is hydrogen, $C_1$–$C_4$-alkyl, phenyl, benzyl or $C_1$–$C_4$-acyl, $R^4$ is hydrogen or methyl, B may be methylene or ethylene in the m or p position or, if A is not carbonyl, may be methyleneoxy, the oxygen atom being bonded to the aromatic, and E is a carboxyl, phosphonic acid or sulfo radical, their physiologically acceptable salts, esters with $C_1$–$C_4$-alcohols or amides or the tetrazol-5-yl radical, have very good oral availability and are very powerful and long-lasting platelet aggregation-inhibition action.

The following compounds are particularly preferred:
4-(1-Oxo-2-phenylsulfonamidoethyl)-phenylacetic acid
3-(1-Oxo-2-phenylsulfonamidoethyl)-phenylacetic acid
4-[2-Oxo-2-(4-chlorophenylsulfonamido)-ethyl]-phenylacetic acid
3-[1-Oxo-2-(4-chlorophenylsulfonamido)-ethyl]-phenylacetic acid
3-(4-[1-Oxo-2-(phenylsulfonamido)-ethyl]-phenyl)-propionic acid
3-(4-[1-Thiono-2-(phenylsulfonamido)-ethyl]-phenyl)-propionic acid
3-(4-[1-Oximino-2-(phenylsulfonamido)-ethyl]-phenyl)-propionic acid
3-(4-[1-Methoximino-2-(phenylsulfonamido)-ethyl)-propionic acid
3-(4-[1-Oxo-2-(4-methylphenylsulfonamido)-ethyl]-phenyl)-propionic acid
3-(4-[1-Oxo-2-(3,4-dimethylphenylsulfonamido)-ethyl]-phenyl)-propionic acid
3-(4-[1-Oxo-2-(2,4,6-trimethylphenylsulfonamido)-ethyl]-phenyl)-propionic acid
3-(4-[1-Oxo-2-(4-ethylphenylsulfonamido)-ethyl]-phenyl)-propionic acid
3-(4-[1-Oxo-2-(4-methoxyphenylsulfonamido)-ethyl]-phenyl)-propionic acid
3-(4-[1-Oxo-2-(4-trifluoromethylphenylsulfonamido)ethyl]-phenyl)-propionic acid
3-(4-[1-Oxo-2-(4-fluorophenylsulfonamido)-ethyl]-phenyl)-propionic acid
3-(4-[1-Oxo-2-(2-chlorophenylsulfonamido)-ethyl]-phenyl)-propionic acid
3-(4-[1-Oxo-2-(2,6-dichlorophenylsulfonamido)-ethyl]-phenyl)-propionic acid
3-(4-[1-Oxo-2-(4-chlorophenylsulfonamido)-ethyl]-phenyl)-propionic acid
3-(4-[1-Thiono-2-(4-chlorophenylsulfonamido)-ethyl]-phenyl)-propionic acid
3-(4-[1-Oximino-2-(4-chlorophenylsulfonamido)-ethyl]-phenyl)-propionic acid
3-(4-[1-Methoximino-2-(4-chlorophenylsulfonamido)-ethyl]-phenyl)-propionic acid
4-(1-Hydroxy-2-phenylsulfonamido-ethyl)-phenylacetic acid
3-(1-Hydroxy-2-phenylsulfonamido-ethyl)-phenylacetic acid
4-[1-Hydroxy-2-(4-chlorophenylsulfonamido)-ethyl]-phenylacetic acid
3-[1-Hydroxy-2-(4-chlorophenylsulfonamido)-ethyl]-phenylacetic acid
3-(4-[1-Hydroxy-2-(phenylsulfonamido)-ethyl]-phenyl-propionic acid
3-(4-[1-Hydroxy-2-(4-chlorophenylsulfonamido)-ethyl]-phenylpropionic acid
4-(1-Hydroxy-2-phenylsulfonamidoethyl)-phenoxyacetic acid
4-[1-Hydroxy-2-(4-chlorophenylsulfonamido)-ethyl]-phenoxyacetic acid
4-[1-Hydroxy-2-(4-fluorophenylsulfonamido)-ethyl]-phenoxyacetic acid
4-[1-Hydroxy-2-(4-chlorophenylsulfonamido)-ethyl]-phenoxymethanesulfonic acid
4-[1-Hydroxy-2-(4-chlorophenylsulfonamido)-ethyl]-phenoxymethanephosphonic acid
4-(1-Methoxy-2-phenylsulfonamido-ethyl)-phenylacetic acid
3-[1-Methoxy-2-phenylsulfonamido-ethyl)-phenylacetic acid
4-[1-Methoxy-2-(4-chlorophenylsulfonamido)-ethyl]-phenylacetic acid
(+)-4-[1-Methoxy-2-(4-chlorophenylsulfonamido)ethyl]-phenylacetic acid
(−)-4-[1-Methoxy-2-(4-chlorophenylsulfonamido)-ethyl]-phenylacetic acid
3-[1-Methoxy-2-(4-chlorophenylsulfonamido)-ethyl]-phenylacetic acid
3-(4-[1-Methoxy-2-phenylsulfonamido-ethyl]-phenyl)-propionic acid
3-(4-[1-Methoxy-2-(4-chlorophenylsulfonamido)-ethyl]-phenyl)-propionic acid
4-(1-Methoxy-2-phenylsulfonamido-ethyl)-phenoxyacetic acid
4-[1-Methoxy-2-(4-fluorophenylsulfonamidoethyl]-phenylacetic acid
4-[1-Methoxy-2-(4-chlorophenylsulfonamidoethyl]-phenoxyacetic acid
(+)-4-[1-Methoxy-2-(4-chlorophenylsulfonamido)-ethyl]-phenoxyacetic acid
(−)-4-[1-Methoxy-2-(4-chlorophenylsulfonamido)-ethyl]-phenoxyacetic acid
4-(1-Acetoxy-2-phenylsulfonamido-ethyl)-phenoxyacetic acid
4-[1-Acetoxy-2-(4-chlorophenylsulfonamido)-ethyl]-phenoxyacetic acid
4-(1-Ethoxy-2-phenylsulfonamido-ethyl)-phenoxyacetic acid
4-[1-Methoxy-2-(N-phenylsulfonyl-N-methylamino)-ethyl]-phenoxyacetic acid.

The novel compounds of the formula I are prepared by (a) reacting a compound of the formula II

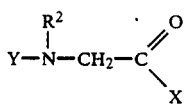

where $R^2$ is hydrogen or $C_1$-$C_4$-alkyl, preferably hydrogen or methyl, X is a leaving group, preferably chlorine, bromine or iodine, and Y is a protective group which can be eliminated by hydrolysis or hydrogenolysis or is a radical $R^1$ having the meanings described for formula I, preferably acetyl, trifluoroacetyl, benzyloxycarbonyl, phenylsulfonyl or (including $NR^2$) a phthalimido group, with a compound of the formula III

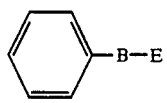

where B and E have the meanings described for formula I but E is preferably carboxyl or methoxy- or ethoxycarbonyl, and, if necessary, eliminating the protective groups from the resulting compound and reacting it with a compound of the formula IV $$R^1—SO_2—X \qquad IV$$

where $R^1$ has the meanings described for formula I and X is a leaving group, preferably chlorine, bromine or iodine, or alkoxy, if necessary reducing the carbonyl group to the alcohol and converting the product into the desired derivatives by known methods, as described in the experimental part by way of example.

The reactions described above, acylation, the elimination of protective groups, introduction of the radical $R^1$—$SO_2$—, reduction and derivatization, can be carried out in any other practical sequence or some of the reactions can be dispensed with.

The Friedel-Crafts acylation is carried out in the presence of a Lewis acid, preferably aluminum chloride, zinc chloride or boron trifluoride, in an inert solvent, preferably methylene chloride, dichloroethane, nitrobenzene, dimethylformamide or a mixture of the abovementioned solvents, at from 0° to 160° C., preferably from room temperature to 80° C.

Elimination of the protective group is carried out by a conventional method, preferably with hydrochloric acid, sulfuric acid or an alkali metal hydroxide in water or in a mixture of water and isopropanol, tetrahydrofuran or dioxane at from 0° to 100° C., but for the benzyloxycarbonyl radical preferably at from 0° C. to room temperature using hydrogen in the presence of a catalyst, such as palladium/carbon, in a solvent, such as water, glacial acetic acid, methanol, ethanol, isopropanol or ethyl acetate.

The sulfonation is likewise carried out by a conventional method in an inert solvent, preferably water, methanol, ethanol, isopropanol, dimethylformamide, dimethyl sulfoxide, pyridine, tetrahydrofuran or a mixture of these solvents, with the addition of a base, preferably sodium carbonate, potassium carbonate, bicarbonate, alkali metal hydroxide, triethylamine or pyridine, at from 0° to 160° C., preferably from 0° to 70° C., and the reduction of the carbonyl to the alcohol is effected with a metal hydride or catalytically activated hydrogen, but preferably at from 0° C. to room temperature with sodium borohydride in water, methanol, isopropanol, acetonitrile or with hydrogen in the presence of palladium/carbon in a solvent, such as water, glacial acetic acid, methanol, ethanol, isopropanol or ethyl acetate.

The compounds of the formula I may furthermore be prepared by (b) reacting octopamine with a compound of the formula IV $$R^1—SO_2—X \qquad IV$$

where $R^1$ has the meanings described for formula I and X is a leaving group, preferably chlorine, bromine or iodine or alkoxy, alkylating the reaction product at the phenolic oxygen, if necessary with activation with trimethylsilyl chloride, with a compound of the formula V $$X—CH_2—E—Y \qquad V$$

where X is a leaving group, preferably chlorine, bromine, iodine, tosylate, mesylate or triflate, and E has the meanings described for formula I, eliminating the protective groups, and converting the product into a derivative of the aliphatic hydroxyl group by a conventional method, as described by way of example in the experimental part.

The abovementioned reactions, sulfonation, activation, alkylation, elimination of protective groups and derivatization, can also be carried out in any other practical sequence or some of the said reactions may be dispensed with.

In this case too, the sulfonation is carried out by a conventional method, preferably as described above. The alkylation at the phenolic oxygen is effected in an inert solvent, preferably water, methanol, ethanol, isopropanol, dimethylformamide, dimethyl sulfoxide, tetrahydrofuran, pyridine or a mixture of the stated solvents, with the addition of a base, preferably an alkali metal hydroxide, sodium carbonate, potassium carbonate, cesium carbonate, ammonium hydroxide or triethylamine, or, after isolation of the phenolate, preferably of the cesium phenolate, in one of the stated solvents at from 0° to 60° C., preferably from 0° to 70° C.

All compounds of the formula I in which A is $CHOR^3$ possess a chiral carbon atom. Consequently, these compounds can be prepared either in optically active form or as a racemic mixture.

If desired, the racemates of the formula I, in which A is $CHOR^3$ and E is carboxyl or sulfo, can be converted into diastereomeric salts by reaction with chiral amines.

Examples of chiral amines are the optically active forms of dehydroabietylamine, brucine, ephedrine, cinchonine, α-methylbenzylamine, 2-aminobutanol, 1-phenylethylamine, 1-cyclohexylethylamine and 3-aminoethylpinane.

The racemic intermediate VI

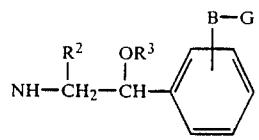

where $R^2$, $R^3$ and B have the meanings described for formula I and G is a tetrazol-5-yl group or the amide or the $C_1$–$C_4$-alkyl ester of a carboxyl group, can likewise be converted into diastereomeric salts by reaction with chiral acids. Examples of chiral acids are the optically active forms of camphor-1-sulfonic acid, α-bromocamphor-π-sulfonic acid, camphoric acid, methoxyacetic acid, tartaric acid, mandelic acid, O,O-diacetyl-, O,O-dibenzoyl- and O,O-di-4-toluyltartaric acid and diacetoneketogulonic acid.

The racemates in the form of their diastereomeric salts can be resolved into their optical antipodes by conventional separation techniques, for example fractional crystallization or column chromatography.

The novel compounds have useful pharmacological properties, in particular a pronounced platelet aggregation-inhibiting action in combination with good oral availability. There is also evidence of an incarbonate, inhibitory action in tumor metastasis and arteriosclerosis.

The novel compounds can be administered in a conventional manner, orally or parenterally (subcutaneously, intravenously, intramuscularly or intraperitoneally).

The dose depends on the age, condition and weight of the patient and on the administration form. As a rule, the daily dose of active compound is from 0.1 to 10, preferably from 0.5 to 5, mg per patient per day in the case of parenteral administration and from 1 to 100, preferably from 5 to 50, mg per patient per day in the case of oral administration.

The novel compounds can be used in conventional solid or liquid pharmaceutical forms, for example as solutions or suppositories. These are prepared in a conventional manner and to do so the active compounds can be mixed with the conventional pharmaceutical auxiliaries, such as tablet binders, fillers, preservatives, tablet disintegrants, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart 1978). The formulations thus obtained normally contain the active compound in an amount of from 0.1 to 99% by weight.

Synthesis scheme using the novel compounds 9a 16a and 17a as Examples

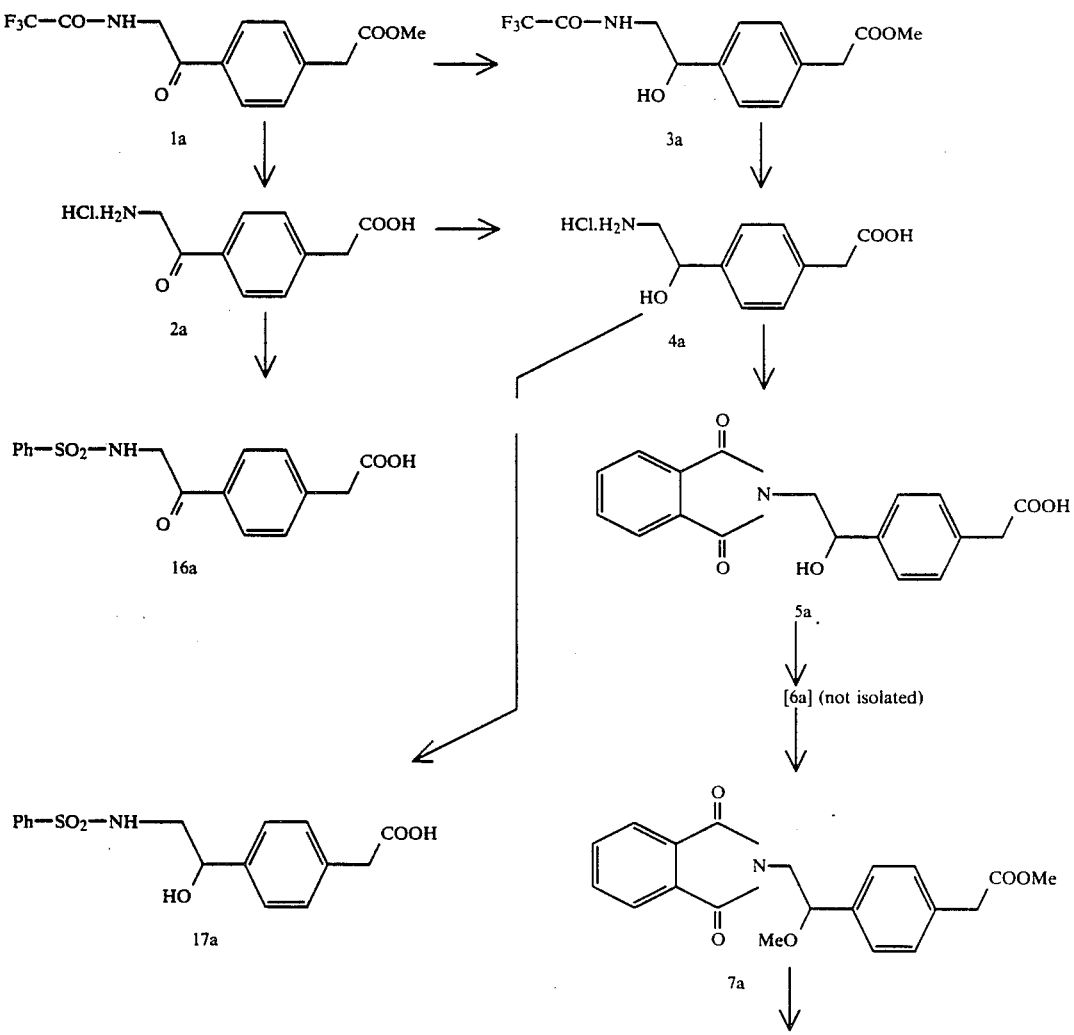

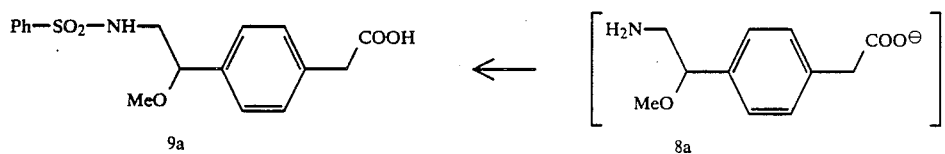
Synthesis scheme using the novel compounds 9a 12a and 13a and 15 as Examples
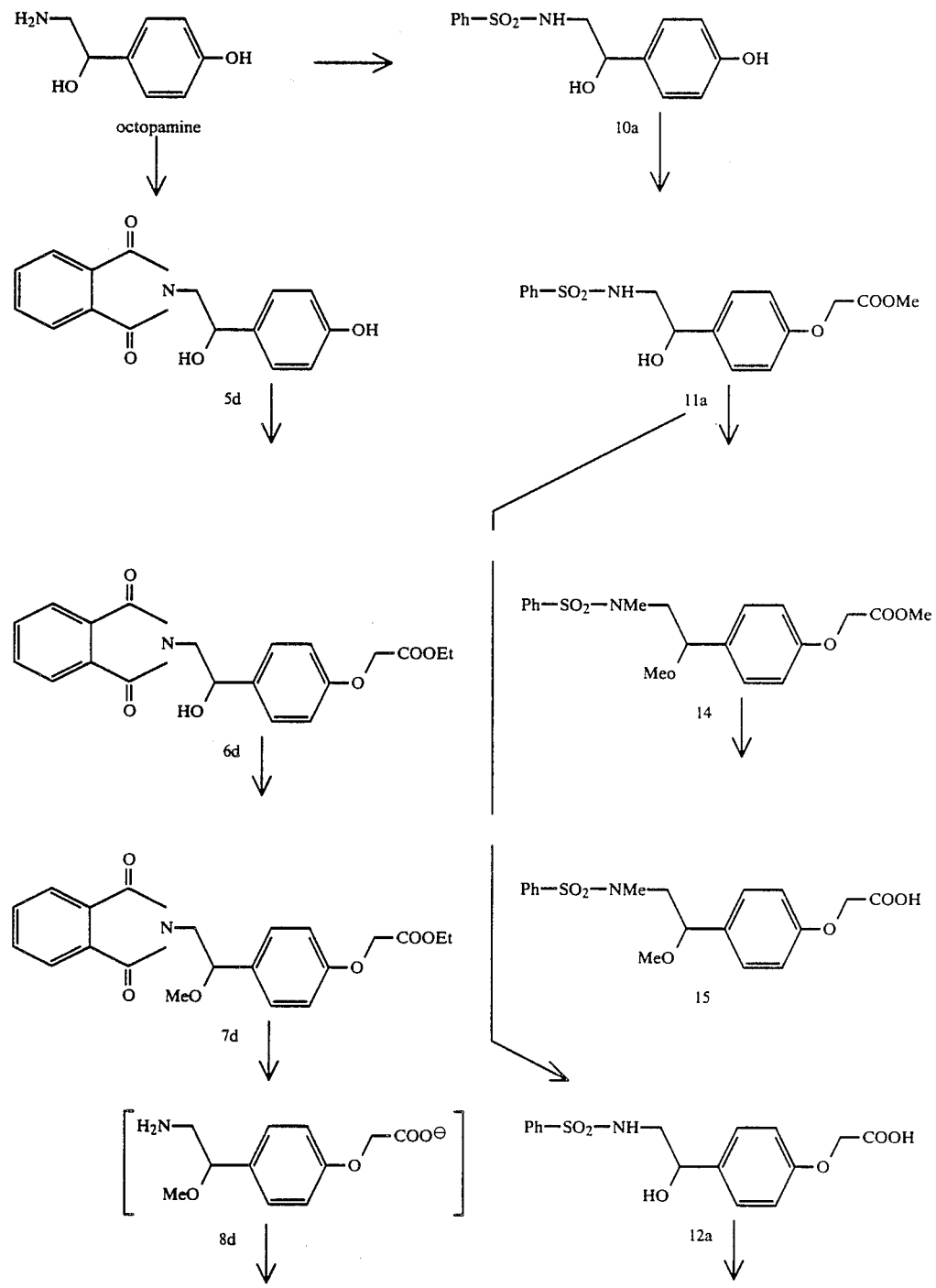

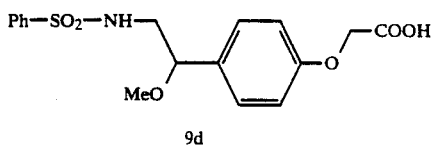

9d

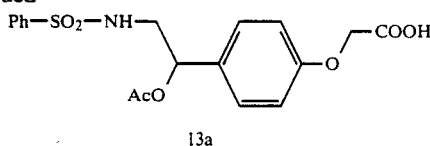

13a

Experimental part

The course of all reactions was monitored by thin layer chromatography on precoated silica gel plates (silica gel 60 $F_{254}$, 5×10 cm, Merck No. 5789). The following solvent mixtures were used as mobile phases, depending on the polarity of the compounds investigated:

(A) Dichloromethane : methanol (40 : 1)
(B) Dichloromethane : methanol : glacial acetic acid (20 : 2 : 1)
(C) n-Butanol : ethyl acetate : $H_2O$ (6 : 2 : 2)
(D) n-Butanol : ethyl acetate : $H_2O$ : pyridine (60 : 6 : 24 : 20)

The products of all reactions described below were investigated by $^1$H-NMR spectroscopy and are in agreement with the stated structure.

Preparation of the intermediates

Methyl 3- and 4-(1-oxo-2-trifluoroacetamidoethyl)-phenylacetate (1a, 1b)

196 g of dimethylformamide were slowly added dropwise to 715 g of aluminum trichloride. After the strongly exothermic reaction had died down, a solution of 1.08 moles of N-(trifluoroacetyl)-glycyl chloride (J. E. Nordlander et al., J. Org. Chem. 49 (1984), 4107) in 1.7 l of dichloromethane and 6 ml of pyridine was slowly added dropwise at 80° C., while stirring. After the evolution of gas had ceased, 161 g of methyl phenylacetate were added dropwise at 70°-80° C. and the mixture was stirred at the same temperature for a further 30 minutes.

The reaction mixture was poured into 6 l of ice water and acidified with concentrated hydrochloric acid, and the precipitated product mixture was filtered off. Crude yield: about 281 g of crystalline solid.

The crude product was digested with 3 times 150 ml of diethyl ether at room temperature. The crystalline residue was filtered off, washed with about 50 ml of diethyl ether and dried under greatly reduced pressure. Yield: 55 g (17%) of methyl 4-(1-oxo-2-trifluoroacetamidoethyl)-phenylacetate (1a); mp. 131°-132° C.

The combined ether filtrates were evaporated to dryness under reduced pressure and the dark residue (226 g) was freed from the colored impurities by flash chromatography (1 kg of silica gel 60, 230 mesh (Merck 7729); column 160×190 mm; gradient elution: 100% of cyclohexane to 80% of cyclohexane/20% of ethyl acetate; reduced pressure from a water pump). 80% of cyclohexane/20% of ethyl acetate eluted 113 g of product which still contained 10-20% of p-component. The p-product was substantially separated off by stirring the crystalline residue from the flash chromatography in an amount of diethyl ether such that 80-90% went into solution. The p-product accumulated in the undissolved residue. After 2-3 successive extractions, p-component was no longer detectable in the $^1$H-NMR spectrum. Yield: 50 g (15%) of methyl 3-(1-oxo-2-trifluoroacetamidoethyl)-phenylacetate (1b); mp. 74°-75° C.

The following were prepared similarly:
methyl 3-(4-[1-oxo-2-trifluoroacetamidoethyl]-phenyl)-propionate (1c), mp. 155°-157° C.;
4-(1-oxo-2-trifluoroacetamidoethyl)-phenoxyacetic acid (1d), mp. 145°-148° C.;
4-(1-oxo-2-trifluoroacetamidoethyl)-phenol (1e), mp. 161°-163° C.

Preparation of ethyl 4-(1-oxo-2-trifluoroacetamidoethyl)-phenoxyacetate (1f)

1.06 g of sodium carbonate or 3.26 g of cesium carbonate were added to a stirred solution of 2.47 g of 4-(1-oxo-2-trifluoroacetamidoethyl)-phenol (1e) in 5 ml of dimethyl sulfoxide at room temperature and, after 30 minutes, 1.83 g of ethyl bromoacetate were introduced. Precipitating crystalline solid gradually made the mixture more viscous. After about 2 hours, the mixture solidified to a thick, unstirrable crystal slurry.

The crystalline mass was suspended in about 100 ml of water, the suspension was filtered and the residue was washed with water.

If the crude product still contains starting material, this can be removed by repeated washing of a solution in ethyl acetate with aqueous sodium carbonate solution.

Yield: 2.58 g (77%) of crystalline solid 1f; mp. 100°-102° C.

Preparation of 4-(2-amino-1-oxoethyl)-phenylacetic acid hydrochloride (2a)

55.0 g of methyl 4-(1-oxo-2-trifluoroacetamidoethyl)-phenylacetate (1a) in 5N hydrochloric acid were refluxed for 2 hours. The slightly cloudy solution was stirred with active carbon, filtered while hot and left to crystallize in an ice bath. The crystalline residue was filtered off, washed with cold water and dried under greatly reduced pressure (27.4 g). The mother liquor was evaporated to dryness under reduced pressure and the residue was digested with isopropanol, filtered off and dried under greatly reduced pressure (6.00 g). The two fractions were of similar quality. Total yield: 33.4 g (80%) of crystalline solid 2a: mp. 259° C. (decomposition).

The following were prepared similarly:
3-(2-amino-1-oxoethyl)-phenylacetic acid hydrochloride (2b), mp. 192° C. (decomposition);
3-[4-(2-amino-1-oxoethyl)-phenyl]-propionic acid hydrochloride (2c), mp. 192°-195° C. (decomposition);
4-(2-amino-1-oxoethyl)-phenoxyacetic acid hydrochloride (2d), mp. 220° C. (decomposition);
4-(2-amino-1-hydroxyethyl)-phenylacetic acid hydrochloride (4a), mp. 202°-203° C.;
3-(2-amino-1-hydroxyethyl)-phenylacetic acid hydrochloride (4b), $R_f$(mobile phase C.)=0.39;
3-[4-(2-amino-1-hydroxyethyl)-phenyl]-propionic acid hydrochloride (4c), mp. 185°-188° C.

Preparation of methyl 4-(1-hydroxy-2-trifluoroacetamidoethyl)-phenylacetate (3a)

2.30 g of sodium borohydride were introduced a little at a time, in the course of 20 minutes, into a stirred solution of 36.0 g of methyl 4-(1-oxo-2-trifluoroacetamidoethyl)-phenylacetate (1a) in 400 ml of isopropanol at room temperature. The reaction mixture was stirred for a further 3 hours until evolution of gas had completely ceased.

The solvent was completely stripped off under reduced pressure, the foamy residue was taken up in 100 ml of water and the solution was extracted with twice 300 ml of diethyl ether. The ether extract was dried, filtered and evaporated to dryness under reduced pressure, and the residue thus obtained was dried under greatly reduced pressure. Yield: 29.0 g (80%) of a greasy solid 3a; $R_f$(mobile phase B)=0.78.

The following were prepared similarly:
methyl 3-(1-hydroxy-2-trifluoroacetamidoethyl)-phenylacetate (3b), mp. 95°–97° C.;
methyl 3-(4-(1-hydroxy-2-trifluoroacetamidoethyl)-phenyl)-propionate (3c), mp. 178° C. (decomposition).

Preparation of methyl 3-(4-[1-hydroxy-2-(trifluoroacetamido)-ethyl]-phenyl]-propionate (3c)

1.00 g of palladium on carbon was added to a solution of 20.0 g of 3-[4-(2-amino-1-oxoethyl)-phenyl]-propionic acid hydrochloride (2c) in methanol and the solution was then hydrogenated for 2 hours under atmospheric pressure and at room temperature.

The catalyst was filtered off, the mother liquor was evaporated to dryness under reduced pressure and the residue was dried under greatly reduced pressure. Yield: 20.0 g (99%) of a crystalline solid (3c); mp. 178° C. (decomposition).

The following were prepared similarly:
methyl 4-(1-hydroxy-2-trifluoroacetamidoethyl)-phenylacetate (3a), $R_f$(mobile phase B)=0.78;
methyl 3-(1-hydroxy-2-trifluoroacetamidoethyl)-phenylacetate (3b), mp. 95°–97° C.;
4-(2-amino-1-hydroxyethyl)-phenylacetic acid hydrochloride (4a), mp. 202°–203° C.;
4-(2-amino-1-hydroxyethyl)-phenoxyacetic acid hydrochloride (4d), mp. 190° C. (decomposition).

Preparation of 4-(1-hydroxy-2-phthalimidoethyl)-phenylacetic acid (5a)

9.85 g of ethyl phthalimidocarboxylate were added a little at a time, while stirring, to a mixture of 10.4 g of 4-(2-amino-1-hydroxyethyl)-phenylacetic acid hydrochloride (4a) and 5.30 g of sodium carbonate in the course of 1 hour at room temperature, the said mixture being virtually completely dissolved in 150 ml of water. The solution was stirred for a further 3 hours, after which it was brought to pH 8 with sodium bicarbonate, washed with ethyl acetate, acidified to pH 3 with sodium bisulfate and left to crystallize while cooling with ice. Yield: 9.80 g (67%) of crystalline solid 5a: mp. 205°–208° C.

The following were prepared similarly:
3-(1-hydroxy-2-phthalamidoethyl)-phenylacetic acid (5b), mp. 107°–109° C.;
3-[4-(1-hydroxy-2-phthalimidoethyl)-phenyl]-propionic acid (5c), $R_f$(mobile phase B)=0.63;
N-phthaloyloctopamine (5d), mp. 207°–209° C.

Preparation of methyl 4-(1-methoxy-2-phthalimidoethyl)-phenylacetate (7a)

9.25 g of 4-(1-hydroxy-2-phthalimidoethyl)-phenylacetic acid (5a) were suspended in about 200 ml of freshly distilled, acid-free and anhydrous dichloromethane, the suspension was cooled to 0° C. and a dry solution of diazomethane in ether was added dropwise under a protective $N_2$ atmosphere until a permanent pale yellow coloration was obtained. The suspended solid went markedly into solution as methyl 4-(1-hydroxy-2-phthalimidoethyl)phenylacetate (6a). Stirring was carried out for 15 minutes at 0° C., after which 0.1 ml of tin(IV) chloride was added under a protective $N_2$ atmosphere, abrupt decoloration of the suspension occurring. During the further dropwise addition of the solution of diazomethane in ether, the remaining suspended solid also went into solution. As soon as the yellow color of the reaction solution became permanent, the addition of the diazomethane solution was stopped, stirring was continued for a further 30 minutes at room temperature and the solution was then decolorized with a few drops of glacial acetic acid. Small amounts of a polymeric impurity were filtered off and the filtrate was evaporated to dryness under reduced pressure. The crystalline residue (9.30 g) was dissolved while hot in 50 ml of isopropanol/ethyl acetate and the solution was added dropwise to 900 ml of ice-cold pentane. Yield: 9.20 g (92%) of crystalline solid 7a: mp. 106°–108° C..

The following were prepared similarly:
methyl 3-(1-methoxy-2-phthalimidoethyl)-phenylacetate (7b), mp. 76°–78° C.;
methyl 3-[4-(1-methoxy-2-phthalimidoethyl)-phenyl]-propionate (7c), mp. 125°–127° C.;
methyl 4-[1-methoxy-2-(N-phenylsulfonyl-N-methylamino)-ethyl]-phenoxyacetate (14), $R_f$(mobile phase A)=0.68.

Preparation of methyl 3-[4-(1-methoxy-2-phthalimidoethyl)-phenyl]-propionate (7c)

6.24 g of silver(II) oxide were added a little at a time, in the course of 1 hour, to a solution, at 0° C., of 4.60 g of 3-[4-(1-hydroxy-2-phthalimidoethyl)-phenyl]-propionic acid (5c) and 3.36 ml of methyl iodide in 45 ml of dimethylformamide. The mixture was stirred in an ice bath and then at room temperature overnight. One equivalent of methyl iodide and silver(II) oxide were added daily for 3 days, after cooling to 0° C.

The reaction mixture was poured into 500 ml of water and extracted with twice 250 ml of diethyl ether. The ether extract was dried, filtered and evaporated to dryness under reduced pressure.

The oily residue (about 5 g) was purified by flash chromatography (silica gel 60, 230 mesh (Merck 7729)). 3.90 g (79%) of the desired product 7c of melting point 125°–127° C. were eluted with 10% of ethyl acetate/90% of cyclohexane. 200 mg (4%) of methyl 3-[4-(1-hydroxy-2-phthalimidoethyl)-phenyl]-propionate (6c) were eluted with 50% of ethyl acetate/50% of cyclohexane.

The following were prepared similarly:
ethyl 4-(1-methoxy-2-phthalimidoethyl)-phenoxyacetate (7d), mp. 100°–105° C.;

ethyl 4-(1-ethoxy-2-phthalimidoethyl)-phenoxyacetate (7e), R$_f$(mobile phase A)=0.79;
methyl 4-[1-methoxy-2-(N-phenylsulfonyl-N-methylamino)-ethyl]-phenoxyacetate (14), R$_f$(mobile phase A)=0.68.

Preparation of 4-(1-methoxy-2-aminoethyl)-phenoxyacetic acid (8d)

A mixture of 8.30 g of ethyl 4-(1-methoxy-2-phthalimidoethyl)-phenoxyacetate (7d) and 83 ml of 25% strength aqueous potassium hydroxide solution was stirred for 6 hours at 100°-110° C.

The aqueous solution was brought to pH 3 with hydrochloric acid, extracted with twice 100 ml of ethyl acetate or diethyl ether, brought to pH 7 with sodium bicarbonate solution and left to crystallize in an ice bath. After filtration and washing, the crystalline residue was dried under greatly reduced pressure. Yield: 2.36 g (49%) of a crystalline solid (8d); mp. 107°-110° C. The mother liquor still contained product.

Alternatively, the aqueous hydrolysis product can be directly used in the sulfonation, after neutralization with hydrochloric acid and without further working up and isolation of the product (cf. Example 9d). Preparation of N-phenylsulfonyloctopamine (10a)

17.6 g of benzenesulfonyl chloride were added dropwise, in the course of 30 minutes, to a stirred solution of 18.9 g of octopamine hydrochloride and 32.8 g of sodium acetate in 200 ml of ethanol at room temperature. The reaction mixture was stirred for a further 30 minutes and then poured into 2 l of water. The precipitated crystalline solid was filtered off, washed, dried, and recrystallized from about 300 ml of methanol (9.95 g). A further 6.95 g of pure product were obtained from the methanolic mother liquor. Yield: 16.9 g (58%) of a crystalline solid 10a: mp. 166°-170° C.

The following were prepared similarly:
N-(4-chlorophenylsulfonyl)-octopamine (10b), mp. 146°-148° C.;
N-(4-fluorophenylsulfonyl)-octopamine (10c), mp. 118°-122° C.

Preparation of the novel compounds

EXAMPLE 1

Preparation of ethyl 4-(1-hydroxy-2-phthalimidoethyl)-phenoxyacetate (6d)

16.3 g of cesium carbonate were introduced into a stirred solution of 14.1 g of N-phthaloyloctopamine (5d) in 30 ml of dimethyl sulfoxide at room temperature. The mixture was stirred for 10 minutes, after which 12.5 g of ethyl bromoacetate were added dropwise in the course of 30 minutes. The reaction mixture was stirred for 4 hours at room temperature, diluted to about 500 ml with water and extracted with twice 100 ml of ethyl acetate. The ethyl acetate solution was dried, filtered and evaporated to dryness under reduced pressure. The oily residue (18.8 g) was digested with 200 ml of diethyl ether, the residue crystallizing. Yield: 13.9 g (75%) of a crystalline solid 6d; mp. 95°-96° C.

The following were prepared similarly:
ethyl 4-(1-hydroxy-2-phenylsulfonamidoethyl)-phenoxyacetate (11a), R$_f$(mobile phase B)=0.68;
ethyl 4-[1-hydroxy-2-(4-chlorophenylsulfonamido)-ethyl]-phenoxyacetate (11b), R$_f$ (mobile phase B)=0.76;
ethyl 4-[1-hydroxy-2-(4-fluorophenylsulfonamido)-ethyl]-phenoxyacetate (11c), R$_f$ (mobile phase B)=0.71.

EXAMPLE 2

Preparation of 4-(1-methoxy-2-phenylsulfonamidoethyl)-phenoxyacetate (9d)

A solution of 4.89 g of 4-(1-methoxy-2-aminoethyl)-phenoxyacetic acid (8d) in 100 ml of water or the neutralized aqueous hydrolysis product of 8.32 g of ethyl 4-(1-methoxy-2-phthalimidoethyl)-phenoxyacetate(7d)(cf. note on Example 8d) was buffered with 4.14 g of potassium carbonate, after which a solution of 4.21 g of benzenesulfonyl chloride in 5 ml of dimethylformamide was added in the course of 30 minutes at room temperature and the reaction mixture was stirred for a further 2 hours.

The aqueous mixture was washed with 100 ml of ethyl acetate, acidified to pH 3 with sodium bisulfate and extracted with twice 150 ml of diethyl ether. The solution in ether was dried, filtered, and evaporated to dryness under reduced pressure.

The oily residue (about 6 g) was purified by flash chromatography (silica gel 60, 230 mesh (Merck 7729)). The desired product eluted between 40% of ethyl acetate/60% of cyclohexane and 100% of ethyl acetate. Yield: 3.66 g (46%) of 9d in the form of an oil; R$_f$(mobile phase B)=0.40; mp. (ammonium salt): 135° C. (decomposition).

The following were prepared similarly:
4-(1-methoxy-2-phenylsulfonamidoethyl)-phenylacetic acid (9a), mp. 121°-122° C.;
3-(1-methoxy-2-phenylsulfonamidoethyl)-phenylacetic acid (9b); amorphous;
3-(4-[1-methoxy-2-phenylsulfonamidoethyl]-phenyl)-propionic acid (9c), mp. (potassium salt): 145° C. (decomposition);
4-[1-methoxy-2-(4-chlorophenylsulfonamido)-ethyl]-phenylacetic acid (9e), mp. 130°-131° C.;
3-[1-methoxy-2-(4-chlorophenylsulfonamido)-ethyl]-phenylacetic acid (9f), amorphous;
3-(4-[1-methoxy-2-(4-chlorophenylsulfonamido)-ethyl]-phenyl)-propionic acid (9g), mp. 149° C. (decomposition);
4-[1-methoxy-2-(4-chlorophenylsulfonamido)-ethyl]-phenoxyacetic acid (9h), mp. 135° C. (decomposition);
4-(1-ethoxy-2-phenylsulfonamidoethyl)-phenoxyacetic acid (9i), mp. 130° C. (decomposition);
4-(1-oxo-2-phenylsulfonamidoethyl)-phenylacetic acid (16a), mp. 156°-160° C.;
3-(1-oxo-2-phenylsulfonamidoethyl)-phenylacetic acid (16b), mp. 135°-137° C.;
4-(1-oxo-2-(4-chlorophenylsulfonamido)-ethyl)-phenylacetic acid (16d), mp. 188°-191° C.;
3-(1-oxo-2-(4-chlorophenylsulfonamido)-ethyl)-phenylacetic acid (16e), mp. 174° C. (decomposition);
3-(4-[1-oxo-2-phenylsulfonamidoethyl]-phenyl)-propionic acid (16c), mp. 150°-155° C.;
3-(4-[1-oxo-2-(4-chlorophenylsulfonamido)-ethyl]-phenyl)-propionic acid (16f), mp. 196°-198° C.;
3-(4-[1-oxo-2-(4-methylphenylsulfonamido)-ethyl]-phenyl)-propionic acid (16g), mp. 166°-167° C.;
4-[1-hydroxy-2-(phenylsulfonamido)-ethyl]-phenylacetic acid (17a), mp. 151°-155° C.;

3-(1-hydroxy-2-phenylsulfonamidoethyl)-phenylacetic acid (17b), mp. (ammonium salt): 59°–65° C.;

4-[1-hydroxy-2-(4-chlorophenylsulfonamido)-ethyl]-phenylacetic acid (17d), mp. 159°–164° C.;

3-[1-hydroxy-2-(4-chlorophenylsulfonamido)-ethyl]-phenylacetic acid (17e), mp. 96°–102° C.;

3-(4-[1-hydroxy-2-phenylsulfonamidoethyl]-phenyl)-propionic acid (17c), mp. 128°–133° C.;

3-(4-[1-hydroxy-2-(4-chlorophenylsulfonamido)-ethyl]-phenyl)-propionic acid (17f), mp. 144°–150 C.;

4-(1-hydroxy-2-phenylsulfonamidoethyl)-phenoxyacetic acid (12a), mp. (potassium salt): 180° C. (decomposition);

4-[1-hydroxy-2-(4-chlorophenylsulfonamido)-ethyl]-phenoxyacetic acid (12b), mp. 113°–116° C.;

4-[1-hydroxy-2-(4-fluorophenylsulfonamido)-ethyl]-phenoxyacetic acid (12c), mp. 114°–117° C..

EXAMPLE 3

Preparation of 4-[1-hydroxy-2-(4-chlorophenylsulfonamido)-ethyl]-phenoxyacetic acid (12b)

10.2 g of ethyl 4-[1-hydroxy-2-(4-chlorophenylsulfonamido)-ethyl]-phenoxyacetate (11b) (prepared similarly to Example 1f) in 25 ml of 1 N NaOH were stirred for 1 hour at room temperature. The solution was washed with ethyl acetate, acified to pH 3 with sodium bisulfate and extracted with twice 50 ml of diethyl ether. The solution in ether was dried, filtered, and evaporated to dryness under reduced pressure. The greasy residue was crystallized by digestion with about 200 ml of diisopropyl ether. Yield: 5.67 g (59%) of a crystalline solid 12: mp. 113°–116° C.

The following were prepared similarly:

4-(1-hydroxy-2-phenylsulfonamidoethyl)-phenoxyacetic acid (12a), mp. (potassium salt): 180° C. (decomposition);

4-[1-hydroxy-2-(4,fltorophenylsulfonamido)-ethyl]-phenoxyacetic acid (12c), mp. 114°–117° C.;

4-[1-methoxy-2-(N-phenylsulfonyl-N-methylamino)-ethyl]-phenoxyacetic acid (15), mp. (ammonium salt): 60°–65° C.

EXAMPLE 4

Preparation of 4-[1-acetoxy-2-(4-chlorophenylsulfonamido)-ethyl]-phenoxyacetic acid (13b)

2 g of 4-[1-hydroxy-2-(4-chlorophenylsulfonamido)-ethyl]-phenoxyacetic acid (12b) were dissolved in a mixture of 10 ml of glacial acetic acid and 10 ml of acetic anhydride. After the addition of 100 mg of N,N-dimethylaminopyridine, the reaction solution was stirred for 8 hours at 50° C.

The solution was completely evaporated under reduced pressure, the residue was dissolved in a little ethyl acetate, the solution was washed with water, dried and filtered, and the filtrate was evaporated down to a volume of about 10 ml and slowly added dropwise to 200 ml of ice-cold petroleum ether. The precipitated crystalline solid was filtered off and dried under greatly reduced pressure. Yield: 1.25 g (57%) of a crystalline solid (13b); mp. 137°–140° C.

The following was prepared similarly:

4-(1-acetoxy-2-phenylsulfonamidoethyl)-phenoxyacetic acid (13a), mp. 216° C. (decomposition)

The following methods were used for investigating the pharmacodynamic properties of the novel products:

1. In vitro inhibition of the aggregation of human, rabbit or canine platelets induced by thromboxane $A_2$ analog (U 46619)

Platelet-rich plasma is obtained from venous citrate blood by centrifuging (160×, 16 min duration at 4° C.). The photometric measurement of the platelet aggregation is carried out by adding $MgCl_2$ (final concentration 10 mmol/1) and U 46619 (final concentration $5 \times 10^{-7}$ mol/1) in a Born aggregometer Mk 3. The maximum change in extinction per second is used as a measure of aggregation. The aggregation-inhibiting activity of the substances is tested after an incubation time of 10 minutes.

Percentage in vitro inhibition of platelet aggregation by some novel compounds at 0.1 mg/l

| Compound | Platelet-rich plasma | | |
|---|---|---|---|
| | Human | Canine | Rabbit |
| 9a | 34% | — | — |
| 9b | 32% | — | — |
| 9d | 26% | — | — |
| 9e | 70% | 65% | 41% |
| 9f | 19% | — | — |
| 9h | 64% | — | — |
| 16a | 58% | — | — |
| 16c | 87% | — | — |
| 16d | 9% | — | — |
| 16f | 96% | — | — |
| 16g | 76% | 81% | 16% |
| 17c | 28% | — | — |
| 17d | 12% | — | — |

2. Ex vivo inhibition of the aggregation of rabbit and canine platelets induced by thromboxane $A_2$ analog (U 46619)

The substances are administered intravenously or orally to groups of from 12 to 16 rabbits (white New Zealand, 2.5–3.2 kg) or from 3 to 5 beagles. At various times after intravenous or oral administration, blood is taken from the animals and platelet-rich plasma is obtained by centrifuging. Aggregation after the addition of U 46619 is measured as described under 1. The ED 50% is determined as the dose which inhibits the platelet aggregation induced by thromboxane $A_2$ analog by 50%.

3. In vivo inhibition of platelet aggregation in the anesthetized rabbit

To test the platelet aggregation-inhibiting action of the substances, an anesthetized rabbit was subjected to laparotomy, after which a few centimeters of the abdominal aorta were carefully exposed and provided with an electromagnetic flow meter probe. About 1 cm distal of the flow meter probe, the vessel is mechanically damaged with the aid of a clamp. A defined narrowing of the vessel with a constrictor of suitable diameter results in cyclic blood flow changes, which are due to the aggregation and subsequent spontaneous detachment of platelets in the region of the stenosis. The reduction in the number and amplitude of these cyclic blood flow variations serves as a measure of the effectiveness of the substances

We claim:

1. A sulfonamide derivative of the formula (I):

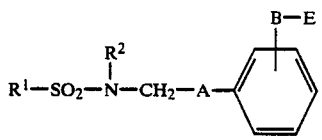

wherein $R^1$ is a $C_1$–$C_4$-alkyl, unsubstituted phenyl or phenyl substituted by halogen, trifluoromethyl or $C_1$–$C_4$-alkyl; $R^2$ is hydrogen or $C_1$–$C_4$-alkyl; A is a bridge member $CHOR^3$, C=O, C=S or C=N—$OR^4$; $R^3$ is hydrogen, $C_1$–$C_4$-alkyl, phenyl, benzyl or $C_1$–$C_4$-acyl; $R^4$ is hydrogen or methyl; B is methylene or ethylene in the m or p position, or if A is not carbonyl, B is methyleneoxy, with the oxygen atom thereof being bonded to the phenyl ring; and E is a tetrazol-5-yl, carboxyl, phosphonic acid or sulfo radical, or the physiologically acceptable salts thereof, or esters thereof with $C_1$–$C_4$-alcohols or amides thereof.

2. A sulfonamide derivative selected from the group consisting of:
4-(1-Oxo-2-phenylsulfonamidoethyl)-phenylacetic acid,
3-(1-Oxo-2-phenylsulfonamidoethyl)-phenylacetic acid,
4-[2-Oxo-2-(4-chlorophenylsulfonamido)-ethyl]-phenylacetic acid,
3-[1-Oxo-2-(4-chlorophenylsulfonamido)-ethyl]-phenylacetic acid,
3-(4-[1-Oxo-2-(phenylsulfonamido)-ethyl]-phenyl)-propionic acid
3-(4-[1-Thiono-2-(phenylsulfonamido)-ethyl]-phenyl)-propionic acid
3-(4-[1-Oximino-2-(phenylsulfonamido)-ethyl]-phenyl)-propionic acid
3-(4-[1-Methoximino-2-(phenylsulfonamido)-ethyl)-propionic acid
3-(4-[1-Oxo-2-(4-methylphenylsulfonamido)-ethyl]-phenyl)-propionic acid
3-(4-[1-Oxo-2-(3,4-dimethylphenylsulfonamido)-ethyl]-phenyl)-propionic acid
3-(4-[1-Oxo-2-(2,4,6-trimethylphenylsulfonamido)-ethyl-phenyl)-propionic acid
3-(4-[1-Oxo-2-(4-ethylphenylsulfonamido)-ethyl]-phenyl)-propionic acid
3-(4-[1-Oxo-2-(4-methoxyphenylsulfonamido)-ethyl]-phenyl)-propionic acid
3-(4-[1-Oxo-2-(4-trifluoromethylphenylsulfonamido)ethyl]-phenyl)-propionic acid
3-(4-[1-Oxo-2-(4-fluorophenylsulfonamido)-ethyl]-phenyl)-propionic acid
3-(4-[1-Oxo-2-(2-chlorophenylsulfonamido)-ethyl]-phenyl)-propionic acid
3-(4-[1-Oxo-2-(2,6-dichlorophenylsulfonamido)-ethyl]-phenyl)-propionic acid
3-(4-[1-Oxo-2-(4-chlorophenylsulfonamido)-ethyl]-phenyl)-propionic acid
3-(4-[1-Thiono-2-(4-chlorophenylsulfonamido)-ethyl]-phenyl)-propionic acid
3-(4-[1-Oximino-2-(4-chlorophenylsulfonamido)-ethyl]-phenyl)-propionic acid
3-(4-[1-Methoximino-2-(4-chlorophenylsulfonamido)-ethyl]-phenyl)-propionic acid
4-(1-Hydroxy-2-phenylsulfonamido-ethyl)-phenylacetic acid
3-(1-Hydroxy-2-phenylsulfonamido-ethyl)-phenylacetic acid
4-[1-Hydroxy-2-(4-chlorophenylsulfonamido)-ethyl]-phenylacetic acid
3-[1-Hydroxy-2-(4-chlorophenylsulfonamido)-ethyl]-phenylacetic acid
3-(4-[1-Hydroxy-2-(phenylsulfonamido)-ethyl]-phenyl-propionic acid
3-(4-[1-Hydroxy-2-(4-chlorophenylsulfonamido)-ethyl]-phenylpropionic acid
4-(1-Hydroxy-2-phenylsulfonamidoethyl)-phenoxyacetic acid
4-[1-Hydroxy-2-(4-chlorophenylsulfonamido)-ethyl]-phenoxyacetic acid
4-[1-Hydroxy-2-(4-fluorophenylsulfonamido)-ethyl]-phenoxyacetic acid
4-[1-Hydroxy-2-(4-chlorophenylsulfonamido)-ethyl]-phenoxymethanesulfonic acid
4-[1-Hydroxy-2-(4-chlorophenylsulfonamido)-ethyl]-phenoxymethanephosphonic acid
4-(1-Methoxy-2-phenylsulfonamido-ethyl)-phenylacetic acid
3-[1-Methoxy-2-phenylsulfonamido-ethyl)-phenylacetic acid
4-[1-Methoxy-2-(4-chlorophenylsulfonamido)-ethyl]-phenylacetic acid
(+)-4-[1-Methoxy-2-(4-chlorophenylsulfonamido)ethyl]-phenylacetic acid
(−)-4-[1-Methoxy-2-(4-chlorophenylsulfonamido)-ethyl]-phenylacetic acid
3-[1-Methoxy-2-(4-chlorophenylsulfonamido)-ethyl]-phenylacetic acid
3-(4-[1-Methoxy-2-phenylsulfonamido-ethyl]-phenyl)-propionic acid
3-(4-[1-Methoxy-2-(4-chlorophenylsulfonamido)-ethyl]-phenyl)-propionic acid
4-(1-Methoxy-2-phenylsulfonamido-ethyl)-phenoxyacetic acid
4-[1-Methoxy-2-(4-fluorophenylsulfonamidoethyl]-phenylacetic acid
4-[1-Methoxy-2-(4-chlorophenylsulfonamidoethyl]-phenoxyacetic acid
(+)-4-[1-Methoxy-2-(4-chlorophenylsulfonamido)-ethyl]-phenoxyacetic acid
(−)-4-[1-Methoxy-2-(4-chlorophenylsulfonamido)-ethyl]-phenoxyacetic acid
4-(1-Acetoxy-2-phenylsulfonamido-ethyl)-phenoxyacetic acid
4-[1-Acetoxy-2-(4-chlorophenylsulfonamido)-ethyl]-phenoxyacetic acid
4-(1-Ethoxy-2-phenylsulfonamido-ethyl)-phenoxyacetic acid
4-[1-Methoxy-2-(N-phenylsulfonyl-N-methylamino)-ethyl]-phenoxyacetic acid.

3. A pharmaceutical composition for the treatment and prophylaxis of thromboembolic disorders, and for the prophylaxis of arteriosclerosis and of metastasis, which comprises an effective amount of the compound of claim 1, and a pharmaceutically acceptable excipient.

4. The pharmaceutical composition of claim 3, in a form suitable for parental administration, which comprises, per unit does, from 0.1–10 mg of said compound and a pharmaceutically acceptable excipient.

5. The pharmaceutical composition of claim 3, in a form suitable for oral administration which comprises, per unit dose, from 1–100 mg of said compound and a pharmaceutically acceptable excipient.

6. A pharmaceutical composition for the treatment and prophylaxis of thromboembolic disorders, and for the prophylaxis of arteriosclerosis and of metastasis, which comprises an effective amount of a compound of claim 2, and a pharmaceutically acceptable excipient.

7. The pharmaceutical composition of claim 6, in a form suitable for parenteral administration, which comprises, per unit dose, from 0.1–10 mg of said compound, and a pharmaceutically acceptable excipient.

8. The pharmaceutical composition of claim 6, in a form suitable for oral administration which comprises, per unit dose, from 1–100 mg of said compound, and a pharmaceutically acceptable excipient.

* * * * *

UNITED STATES PATENT AND TRADEMARK OFFICE
CERTIFICATE OF CORRECTION

PATENT NO. : 4,999,345
DATED : March 12, 1991
INVENTOR(S) : Bernhard Schmied et al.

It is certified that error appears in the above-identified patent and that said Letters Patent is hereby corrected as shown below:

On the title page, item [75] Inventors: change "Hand D. Lehmann to --Hans D. Lehmann--.

Signed and Sealed this

Fourth Day of May, 1993

*Attest:*

MICHAEL K. KIRK

*Attesting Officer*    *Acting Commissioner of Patents and Trademarks*